United States Patent
Vu

[11] Patent Number: 5,480,646
[45] Date of Patent: Jan. 2, 1996

[54] PAD FOR APPLYING MEDICAMENTS

[76] Inventor: Van N. Vu, 72 Maple Ave., Atherton, Calif.

[21] Appl. No.: 322,265

[22] Filed: Oct. 12, 1994

[51] Int. Cl.$^6$ .............................. A61K 9/14; A61F 13/00
[52] U.S. Cl. ............................................ 424/443; 424/489
[58] Field of Search .......................... 252/107; 424/489, 424/490, 488; 36/43

[56] References Cited

U.S. PATENT DOCUMENTS

| | | | |
|---|---|---|---|
| 4,095,353 | 6/1978 | Foldes | 36/11.5 |
| 4,324,785 | 4/1982 | Stevens | 424/195 |
| 4,510,699 | 4/1985 | Nakamura | 36/43 |
| 4,533,351 | 8/1985 | Waslikuln | 604/293 |
| 4,668,419 | 5/1987 | Moseman | 252/107 |
| 5,022,168 | 6/1991 | Jepson | 36/43 |
| 5,035,068 | 7/1991 | Biasi | 36/43 |
| 5,067,256 | 11/1991 | Darly | 36/69 |
| 5,154,682 | 10/1992 | Kellerman | 36/3 |
| 5,195,254 | 3/1993 | Tung | 36/3 |
| 5,261,109 | 11/1993 | Williford | 36/43 |
| 5,261,169 | 11/1993 | Williford | 36/43 |
| 5,397,584 | 3/1995 | Aung et al. | 426/327 |

OTHER PUBLICATIONS

CRC Medicinal Herbs, by J. Duke CRC Press, Boca Raton, Fla. pp. 127, 470.
Encyclopedia of Chemical Technology, v. 9 pp. 576, 577, Interscience Encyclopedia, N.Y.

*Primary Examiner*—Thurman K. Page
*Assistant Examiner*—William E. Benston, Jr.
*Attorney, Agent, or Firm*—Robert Samuel Smith

[57] ABSTRACT

A pad lined with a mixture of cinnamon, aloe wood and anise star powders having a pervious surface for contacting the skin and exposing the skin to emanations from the powders. The pad has a plurality of chambers which contain portions of the powder and maintain the even distribution of the powder as a lining in the pad. In one embodiment, The pad is an insole worn in footwear. In another embodiment, the pad is provided with bands for strapping the pad to various areas of the body.

15 Claims, 2 Drawing Sheets

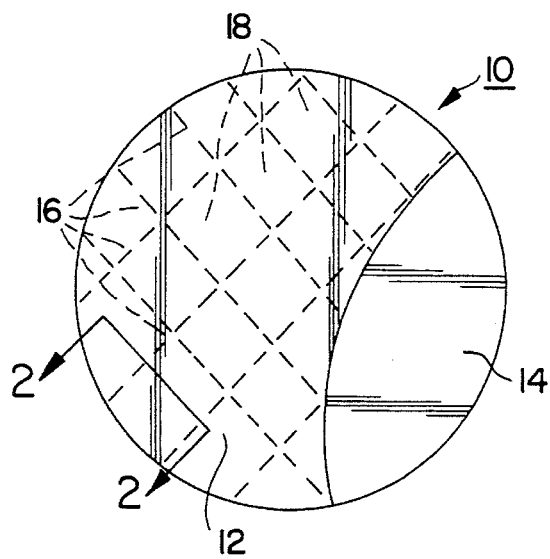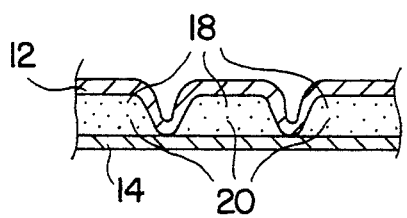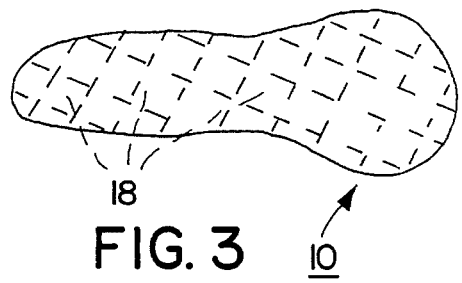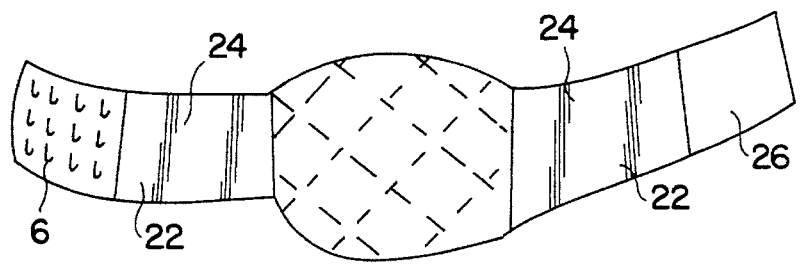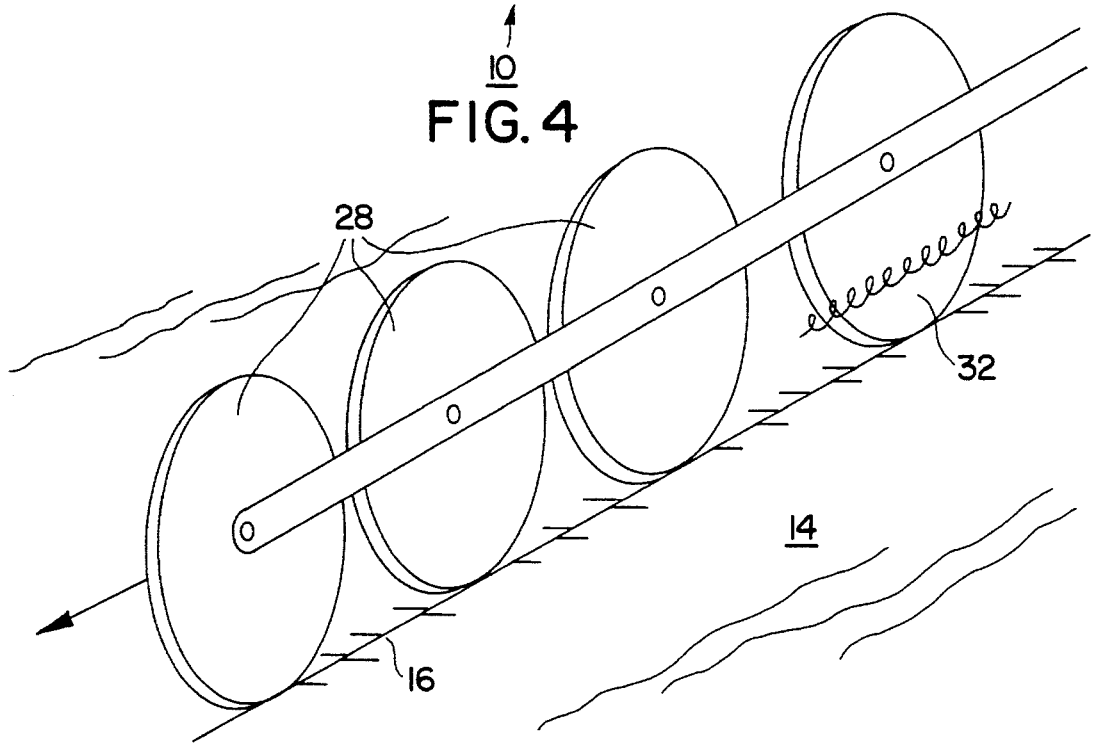

PAD FOR APPLYING MEDICAMENTS

FIELD OF THE INVENTION

This invention relates to pads containing medicaments for application against the surface of the body and particularly to the soles of the feet.

PRIOR ART AND INFORMATION DISCLOSURE

The external application of herbal based formulations and/or various forms of massage have long been traditional methods of treatments for a long list of complaints including sore muscles, aching joints, respiratory congestion, external bacterial or fungal attacks, etc.

Acupressure therapy, adopted by many, is based on the premise that pressure applied to certain areas of the body is effective in relieving a number of complaints, each complaint being specific to the area of the body to which pressure is applied. In particular, pressure applied to the sole of the foot is believed to be effective in relieving a number of common complaints.

Specially designed insoles have been disclosed to bring about relief automatically as the wearer walks.

For example, U.S. Pat. No. 4,095,353 to Foldes discloses a one piece flexible plastic or rubber sandal having flexible thin points which flex under the weight of the foot.

U.S. Pat. No. 4,510,699 to Nakamura discloses an insole, the material for which is made from an elastomer having a gum-like elasticity.

U.S. Pat. No. 5,022,168 to Jeppson et al discloses a fabric insole for insulating the foot.

U.S. Pat. No. 5,035,068 to Biasi discloses an insole being an impervious flexible base with a plurality of upwardly extending compressible support columns having upper ends which yieldingly support the foot.

U.S. Pat. No. 5,067,256 to Darby discloses a heel cup of molded rubber or incompressible flexible plastic with support pegs to define and support the arch.

U.S. Pat. No. 5,154,682 to Kellerman discloses a low friction insert with an array of detachable discrete cushions.

U.S. Pat. No. 5.195.254 to Tyng discloses an insert sole including a resilient pad having recesses with air bags.

U.S. Pat. No. 5,203,793 to Lyden discloses an insole comprising a conformable material of liquid matter substantially comprising solid matter after a working time.

There also exists extensive literature describing the use of various ingredients of herbal origin to relieve the type of problem listed above.

For example, U.S. Pat. No. 4,324,785 to Stevens discloses a powder including cayene pepper, ginger, mustard and an aromatic substance for imparting a feeling of warmth particularly to the feet.

The following information pertaining to Anise star and Aloe Wood is taken from the "Encyclopedia of Chemical Technology" v.1, pp. 576, 577 published by the Interscience Encyclopedia, Inc. New York and is hereby incorporated as reference in this specification.

Anise, Star is distilled from the star shaped fruit of Illicum verum, grown in Indo-China. Its most important constituent is is anethole, occurring to the extent of about 90%. The oil of anise, star is used as an expectorant and medicinal flavoring agent, treatment of colic and as a flavoring agent in bakery goods, candies, chewing gums, tobacco and alcoholic liquors.

Aloewood (or Rosewood) is a source of an oil whose principle constituent is "linalool" (90%), an oil used as an artificial flavoring and in soaps and perfumes. Aloewood, which comes from an Indochinese tree, is not to be confused with "Aloe", a juice or gel which comes from the leaves of the Aloe plant and is used as a cathartic.

The following information regarding Cinnamon is taken from the CRC Handbook of Medicinal Herbs by J. Duke, CRC Press Inc., Boca Raton, Fla. page 127.

The bark (of Cinnamon) is used in food, dentrifices, incenses and perfumes. Cinnamon bark oil, distilled from chips and bark, is used in perfumes, soaps, cordials and in drug and dental preparations. Cinnamon leaf oil, distilled from dried green leaves, is a powerful germicide and is also used in perfumes spices and in the synthesis of vanilla. Cinnamon oil is antifungal, antiviral, bactericidal and lavicidal.

Insoles have been disclosed which contain medicaments for various purposes. U.S. Pat. No. 4,533,353 to Washkuhn discloses impregnation of foam rubber or plastic insole with an active antibacterial and antifungal agent.

U.S. Pat. No. 5,261,169 to Williford discloses an insole having a resilient layer with a plurality of reservoirs containing powder which is released by pressure from the foot.

THE INVENTION

OBJECTS

It is an object of this invention to provide a method and a device for exposing various surfaces of the body to emanations from a novel powder composition of this invention in order to bring relief from various complaints including muscle soreness, aching joints, poor circulation of the blood, cold sweats, body odor (especially of the feet), etc.

SUMMARY

This invention is directed toward a novel combination of powders which includes cinnamon in the amount of about 75% by weight, Aloe Wood in the amount of about 15% by weight, Anise Star in the amount of about 10% by weight. All of these constituents are aromatic indicating that the cinnamon oil, the oil of anise star and the linalool oil of aloe wood all emanate from the powder composition.

The composition is administered by pressing a pad against an appropriate surface area of the body wherein the pad contains the composition as a lining. The surface of the pad against the skin is a thin pervious panel such as (preferably) cotton fabric having a weave selected to prevent particles of powder passing therethrough but permitting emanations from the powder to pass therethrough and the surface of the pad opposite the cotton is an impervious flexible panel such as vinyl. The pervious panel is secured to the vinyl panel along lines which form edges of closed chambers over the entire surface of the pad. The chambers are filled with the powder composition. The skin, pressed against the pervious side of the pad, is thereby exposed to the emanating constituents of the composition.

In one embodiment, the pad is an insole that is fitted inside the user's shoe or sock. In another embodiment, the pad is held firmly against the body by a strap which is a combination elastic and hook and eye material. "Hook and eye material" is a well known product sold under the trade name VELCRO

The pad with attached strap is tailored according to the part of the body against which it is pressed such as the neck, wrist, back, etc. All of these versions of the pad are within the scope of the invention.

DRAWINGS

FIG. 1 shows the pad of this invention.

FIG. 2 shows a cross section of a pad.

FIG. 3 shows a pad of this invention shaped as an insole.

FIG. 4 shows a pad attachable to the body by a combination VELCRO and elastic band.

FIG. 5 shows an apparatus for stitching or heat welding the vinyl panel to the fabric panel thereby defining chambers in the pad, each chamber containing a portion of the composition.

DESCRIPTION OF A PREFERRED EMBODIMENT

Figure 6:
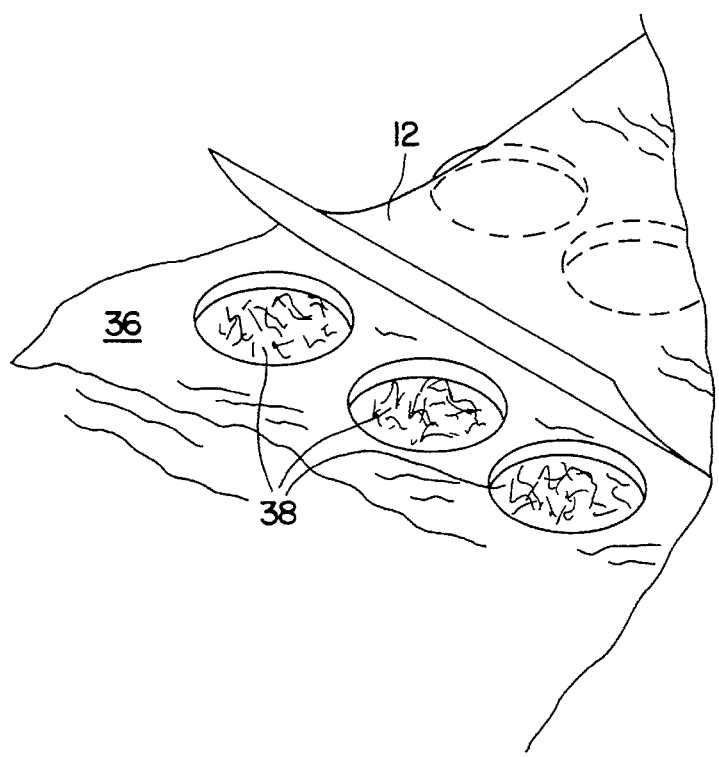
FIG. 6 shows a pad with an intermediate panel.

Turning now to a discussion of the drawings, FIG. 1 shows the pad 10 of this invention including a cotton fabric panel 12 partially cut away to show a vinyl panel 14. The two panels are stitched together along stitch lines 16 such as to form chambers 18. The chambers are filled with a powder composition that includes cinnamon, about 75% by weight, aloe wood, about 15% by weight and anise star, about 10% by weight.

FIG. 2 is a sectional view showing a chamber containing powder 20 and bounded by an impervious vinyl panel 14 and a pervious cotton panel 12.

Although this composition is preferred, compositions are effective which are in the range 15% to 25% aloe wood, 10% to 20% anise star, and 55% to 75% cinnamon.

Although I do not wish to be bound by theory, it is believed that the effectiveness of the composition in achieving the objects of the invention is based on diaphoretic properties of the cinnamon which open the pores of the skin to permit greater exposure to emanations from the lignaloe oil of the aloewood and anathole oil of anise star.

Comparison of the stitched pad of the present invention to comparably sized pads of the prior art having an intermediate panel with apertures shows that the pad of the present invention provides a greater exposure of the powder composition to the skin. Furthermore, when the pad is worn as an insole, pressure of the foot directly against the fabric covered chamber containing the powder composition is greater with the pad having the stitched construction than when the chamber is defined as an aperture in an intermediate panel of incompressible material because (with the latter panel) much of the force from the foot will be exerted against the web of the intermediate panel.

The pad is pressed into intimate contact with the skin by one of several constructions depending on the area of the body. FIG. 3 shows a pad 10 of this invention shaped as an insole 3 that may be inserted into a shoe. In this situation, the entire sole of the foot is pressed against the pad and each chamber 18 is a pressure location where the lump of fabric covered composition is forced into intimate contact with an area of the sole of the foot as the user walks.

FIG. 4 shows another construction for holding the pad in intimate contact with an areas of the skin other than the soles of the feet. There is shown the pad 10 having the stitched double layer construction of FIG. 1 and a pair of bands 22, each band having an end attached to an edge of the pad opposite the other band. Each band has an elastic section 24 attached to an edge of pad 10 and an end 26 covered with "hook and eye" (VELCRO) material arranged to engage the end of the other band.

The dimensions of the pad 10 and the length of the bands 22 are selected according to the area of the body to be treated. Therefore, the scope of the invention includes a pad with bands dimensioned for strapping around the wrist, around the abdominal area for supporting the pad against the back or abdomen, around the neck for supporting the pad against the back of the neck, around the thigh, etc. The elastic construction of the band provides for adjustable intimate forced contact of the active surface of the pad 10 against the body.

Other variations of this invention may be contemplated which are within the scope of this invention.

For example, an open cell foam panel may be considered in place of the fabric panel.

The lines of connection between the fabric panel and the vinyl panel forming the chambers may be formed by adhesive or heat sealing.

An apparatus for forming heat sealed lines is shown in FIG. 5 to include one or more doctor wheels 28 which form the line 16 (crease) in the assembled vinyl 14 and fabric panel (not shown). The lines 16 define the chambers 18 so as to separate portions of the powder composition into separate chamber groups and allow a heated wheel 32 (or stitching needle) to pass along the line and join the two panels.

Another panel of a material that is selected for its comfortable "feel" against the skin such as nylon way be secured to the pad on either one or both sides of the pad.

The novel powder composition of this invention may be applied directly such as by dusting the powder into a shoe.

As shown in FIG. 6 when it is desired to apply the active area of the pad to only a well defined area of the body, the pad may be constructed with an intermediate panel 36 having apertures 38 between an impervious panel (not shown) and a pervious panel 12 In this construction, the intermediate panel 36 is preferably a compressible foam so that the web of the intermediate layer does not appreciably diminish the force of the skin against the portion of composition in each chamber 38.

Figure 7:
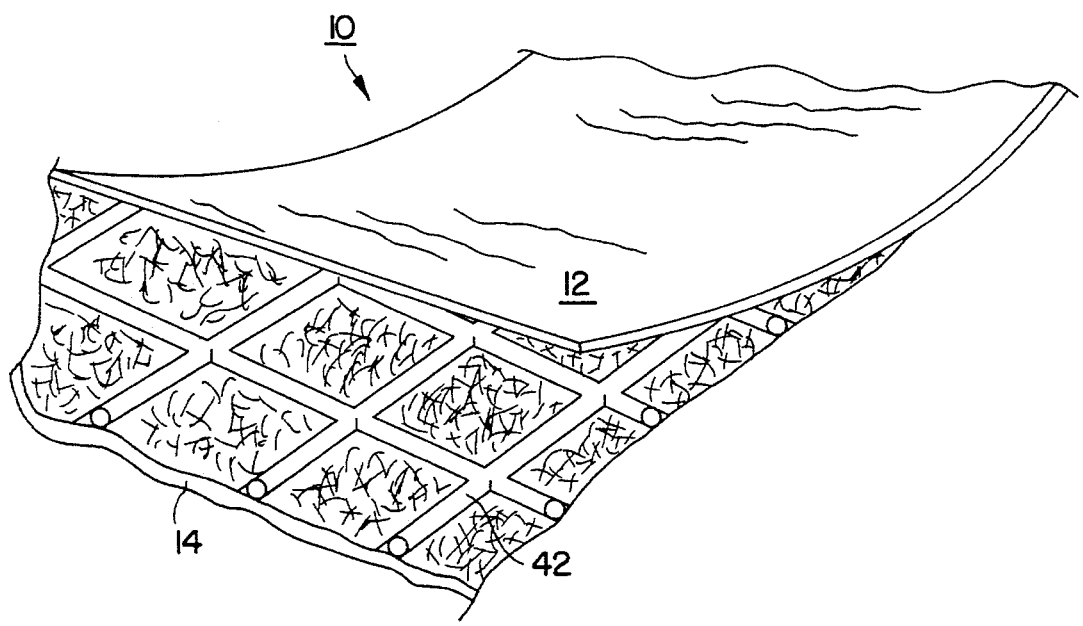
FIG. 7 shows a pad with an intermediate net.

FIG. 7 shows a construction of the pad 10 in which the chambers are formed by a plastic wire net 42 interposed between the fabric layer 12 and the vinyl layer 14.

In view of these and other contemplated variations, I therefore wish to define my invention by the appended claims.

I claim:

1. A pad for inducing diaphoretic response to an area of the skin which comprises:

an impervious flexible panel;

a pervious flexible panel joined to said impervious panel such as to form a plurality of closed chambers;

said pervious panel having an open structure such that powder particles are prevented from passing there through but through which vapors emanating from said powders can pass therethrough;

each chamber bounded by an area of said pervious panel opposite an area of said impervious panel;

a portion of a powder composition in each chamber from which said closed chamber said portion cannot escape but from which emanations from said powder, can escape;

said powder composition being a mixture of powders of Aloe wood in an amount of 15% to 25%, anise star in an amount ranging from 10% to 20%, and Cinnamon in an amount from 55% to 75%;

means for pressing said pervious side of said pad against said area;

said means being one of:
 (i) said pad having a shape of an insole adapted for positioning in a shoe against a sole of a foot;
 (ii) at least one band arranged in operable combination with said pad adapted for strapping said pad to a part of a human body with said pervious panel forced against said area of skin;

whereby pressure on said pad actuates vapors to emanate from said powder contained in said plurality of chambers through said pervious panel to said area of skin.

2. A pad as in claim 1 wherein said pervious flexible panel is cotton fabric.

3. A pad as in claim 1 wherein said impervious flexible panel is a vinyl plastic.

4. A pad as in claim 1 wherein said pervious panel is an open cell foam plastic.

5. A pad as in claim 1 wherein said pervious flexible panel is joined to said impervious flexible panel by stitches along lines defining edges of said chambers.

6. A pad as in claim 1 wherein said pervious flexible panel is joined to said impervious flexible panel by an adhesive along lines defining edges of said chambers.

7. A pad as in claim 1 wherein said pervious flexible panel is joined to said impervious flexible panel by heat sealing along lines defining edges of said chambers.

8. A pad as in claim 1 wherein said part of a human body is selected from a group of parts which consists of a neck, a back, an arm, a leg, an ankle, an and an abdomen.

9. A pad as in claim 1 wherein said band comprises one elastic strap having one end secured to one edge of said pad and hook or eye material on another end of said one strap and another elastic strap having one end secured to another edge of said pad and having eye or hook material on another end of said another elastic strap arranged to engage said another end of said one strap.

10. A pad as in claim 1 which comprises an intermediate panel interposed between said pervious panel and said impervious panel and having a plurality of apertures which define said plurality of chambers between said pervious and impervious panels.

11. A pad as in claim 10 wherein said intermediate layer comprises compressible foam.

12. A pad as in claim 1 which comprises a plastic wire net interposed between said pervious panel and said impervious panel;

said plastic wire net having apertures defining edges of said plurality of chambers;

said pervious panel laminated to one side of said plastic wire net and said impervious panel being laminated to another side of said wire net.

13. An apparatus for heat sealing two panels separated by a layer of powder composition along a line on said panels which comprises;

at least one wheel adapted for creasing said panels along said line;

a heated wheel adapted to roll in said crease.

14. A powder to be applied to the human body and having diaphoretic properties which consists of cinnamon, aloe wood, anise star.

15. A powder as in claim 14, wherein said powder consists of cinnamon in the range of about 55% to 75% by weight, aloe wood in the range of about 15% to 25% by weight and anise star int the range from about 10% to 20% by weight.

* * * * *